United States Patent [19]

Mathey et al.

[11] 4,173,706
[45] Nov. 6, 1979

[54] PROCESS FOR PRODUCING FLUORINATED ORGANIC COMPOUNDS CONTAINING A DIFLUOROMETHYLENE GROUP FROM COMPOUNDS COMPRISING AT LEAST ONE CARBONYL FUNCTION

[75] Inventors: François Mathey; Jean Bensoam, both of Ballancourt, France

[73] Assignee: Institute National de Recherche Chimique Appliquee, Paris, France

[21] Appl. No.: 894,080

[22] Filed: Apr. 6, 1978

Related U.S. Application Data

[63] Continuation of Ser. No. 533,272, Dec. 16, 1974, abandoned, which is a continuation-in-part of Ser. No. 185,362, Sep. 30, 1971, Pat. No. 3,878,296.

[30] Foreign Application Priority Data

Dec. 14, 1973 [FR] France .................................. 7344885

[51] Int. Cl.$^2$ ...................... C07B 9/00; C07C 87/28; C07C 103/22; C07C 125/06
[52] U.S. Cl. .............................. 560/30; 260/326 HL; 260/465 G; 260/544 D; 260/544 P; 260/558 R; 260/558 D; 260/570 R; 260/570.9; 260/599; 260/646; 260/649 F; 260/651 F; 260/69.1; 544/176; 560/27; 560/31; 560/101; 560/109; 560/110; 562/491; 562/493; 568/809; 568/812

[58] Field of Search ........... 260/515 A, 518 A, 544 P, 260/544 D, 570 R, 570 A, 558 R, 558 P, 599, 618 D, 694; 544/176; 560/27, 30, 31, 101, 109, 110; 562/491, 493; 568/809, 812

[56] References Cited

U.S. PATENT DOCUMENTS 2,862,974  12/1958  Sieglitz et al. .................... 260/649 F
3,812,177  5/1974   Engelhardt et al. ........ 260/618 D X

OTHER PUBLICATIONS

Mathey et al., Tetrahedron, vol. 27 (1971) pp. 3965–3969.
Yagupolskii, Zhurnal Olshchei Khimii, vol. 23 (1953) pp. 988–991.
Inukai et al., Chemical Abstracts, vol. 61 (1964) 9418.
Sandler et al., Organic Functional Group Preparations, Academic Press, New York (1968) pp. 152,247 & 274–276.
Wagner et al., Synthetic Organic Chemistry, John Wiley & Sons, New York (1953) p. 645.

Primary Examiner—Richard Raymond
Attorney, Agent, or Firm—Karl W. Flocks

[57] ABSTRACT

A novel process for producing fluorinated organic compounds containing a difluoromethylene group, essentially characterized by reacting organic compounds containing a carbonyl function with molybdenum hexafluoride at room temperature and under atmospheric pressure.

9 Claims, No Drawings

PROCESS FOR PRODUCING FLUORINATED ORGANIC COMPOUNDS CONTAINING A DIFLUOROMETHYLENE GROUP FROM COMPOUNDS COMPRISING AT LEAST ONE CARBONYL FUNCTION

FIELD OF INVENTION

This is a continuation of application Ser. No. 533,272, filed Dec. 16, 1974, now abandoned, which in turn is a Continuation-in-Part of copending application Ser. No. 185,362 filed Sept. 30, 1971, now U.S. Pat. No. 3,878,246.

The present invention relates to a new process for fluorinating organic compounds containing at least one ketone or aldehyde group in order to produce fluorinated organic compounds containing a difluoromethylene group. The present invention also relates to procedures for preparing substituted α,α-difluoroalkylbenzene compounds as well as to the compounds resulting from same.

BACKGROUND

Fluorinated organic compounds are well known and in recent years have gained technical importance in view of their particular chemical and physical properties such as good thermal resistance and resistance to oxidation. They are also in great demand in pharmaceutical chemistry. For these reasons, simple and economical processes have been sought for obtaining these products.

The fluorination processes up to the time of parent application Ser. No. 185,362, now U.S. Pat. No. 3,878,246 used reagents which are highly toxic or not easily obtainable, or which may even require the use of special equipment. They often lead to secondary polymerization and decomposition reactions. In particular, fluorination of carbonyl groups into difluoromethylene groups can be performed by the use of the reagent $SF_4$ (see U.S. Pat. No. 2,859,245). In addition to the fact that $SF_4$ is an extremely toxic gas, the process is difficult to perform. In fact, the solid or liquid reagents must be fed into a hastelloy autoclave under an atmosphere of nitrogen; thereafter one must cool to $-80°$ C., sweep the gases, introduce $SF_4$, react the mixture at the desired temperature (approx. $100°$ C.) under autogenous pressure, then cool to $-80°$ C. and finally open the autoclave. The products are then separated. Moreover, it should be pointed out that there is a significant loss of the reagent $SF_4$ the molar excess of which is between 1.5 and 4 or even more.

SUMMARY

In parent application Ser. No. 185,362, the subject matter of which is hereby incorporated by reference, there is described a process of preparing fluorinated organic compounds that contain the difluoromethylene group, from compounds that contain at least one ketone or aldehyde group. This process, which is applicatle to the production of the compounds of the present invention, comprises reacting the organic starting compounds containing the ketone or aldehyde function with molybdenum hexafluoride, at ambient temperature and at atmospheric pressure and in anhydrous solvent medium in the presence of $BF_3$ or any other fluoride ion acceptor of the strong Lewis acid type.

There are various types of compounds which may be fluorinated in accordance with such process. In most of the examples of the parent application Ser. No. 185,362, there are no other functional groups in the organic starting compound to react with the $MoF_6$ except the ketone or aldehyde group desired to be fluorinated.

It is an object of the present invention to provide compounds of the substituted α,α-difluoroalkylbenzene type of the formula

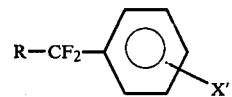

wherein X' designates a substituent inert with respect to $MoF_6$.

But there are also various types of compounds which cannot be fluorinated in accordance with such process e.g. compounds containing, besides the ketone or aldehyde groups, other functional group reacting with $MoF_6$.

It is therefore another object of the invention to provide a process for preparing new compounds of the substituted α,α-difluoroalkylbenzene type of the formula

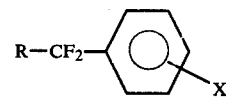

wherein X designates a substituent which reacts with $MoF_6$.

In such a case the starting compound cannot be:

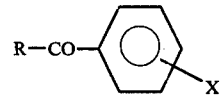

because reaction with $MoF_6$ would yield in a complex and unseparable mixture of various fluorinated products.

Now the applicants have solved this problem by choosing a starting compound of the formula

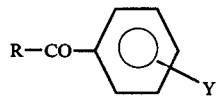 (II)

wherein Y is such that:

(1) It does not react with $MoF_6$ so that the fluorination step leads to the product

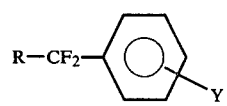 (III)

(2) It allows the conversion of Y to X without altering the remaining part of the molecule i.e. it allows to perform the reaction:

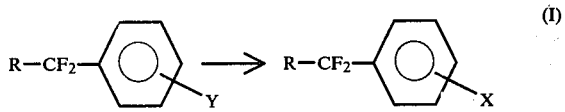  (I)

Thus, one obtains the desired product which could not be prepared in a single step process.

The above mentioned objects are achieved in accordance with this invention by reacting, the starting organic compound with substantially anhydrous molybdenum hexafluoride as fluorinating agent, under substantially anhydrous conditions, in solution in a solvent inert with respect to the reactants, in a glass vessel at a temperature of about −20° C. to about +40° C. conveniently under atmospheric pressure and under an inert atmosphere, the molar ratio of MoF$_6$ to (C=O) group being about 1; and then, as the case may be, converting the product of the fluorination reaction II to the desired product (I) containing a group X which would have reacted with MoF$_6$ during the fluorination.

The new compounds of the type mentioned above are stable and can be used especially as intermediate products in organic synthesis, in particular in the field of pharmaceutical industry. It is in fact well known that modern sophisticated pharmaceuticals often contain fluorinated groups so that the products of the above type are potentially interesting. But these pharmaceuticals are outside the scope of the present invention.

According to the invention, the compounds correspond to the generic formula:

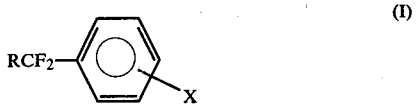  (I)

where X, which may be situated in ortho, meta or para position, and preferably in the para or meta position, is —CN, —NO$_2$, —F, —Cl, —COOH, —COCl, —CH$_2$OH, —CONH$_2$, —CHO,

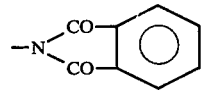

—COOR', —CONR'$_2$, CO—R'', —NHCOOR', —CH$_2$NH$_2$, —COO(CH$_2$)$_n$NR'$_2$; n is 2 or 3; R' is an alkyl or aryl radical, preferably lower alkyl or phenyl; R'' is a heterocyclic amine of morpholine type; R is an alkyl or aryl group, preferably lower alkyl or phenyl, and may also be hydrogen in the case where X does not represent —NO$_2$, —F, —Cl, —COOR', —CHO, —NHCOOR', or

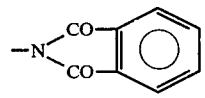

It has actually been discovered that the substituent X, in this type of compound, leads to stabilization of the molecule and, for this purpose, it preferably consists of an electrophilic group.

When the desired compound

  (I)

contains an X group which reacts with the MoF$_6$, the starting compound choosen is

  (II)

wherein Y is selected so that it can easily be later converted into X by these conventional methods of organic synthesis which do not affect the remaining part of the molecule.

DETAILED DESCRIPTION OF PREFERRED EMBODIMENTS

The organic compounds used in the present process at the fluorination stage are all ketones and aldehydes whether aliphatic, cyclic or aromatic the only condition at this stage being that the molecule concerned does not contain any other group capable of reacting with MoF$_6$. The groups capable of reacting with MoF$_6$ are Lewis bases (basic ethers, amines, groups with ethylenic or acetylenic bonds), or groups possessing labile hydrogen atoms (acids, alcohols, phenols, primary and secondary amides and the like). Indeed MoF$_6$ is a rather strong Lewis acid and thus will react with Lewis bases.

MoF$_6$ is also an oxidizing agent and like the higher halides of Mo, W and the like, it is readily hydrolized; accordingly it will react with double or triple carbon-carbon bonds and with compounds having labile hydrogen atoms as previously mentioned.

In the case of preparing substituted α,α-difluoroalkylbenzenes, wherein the substituent is a —CONH$_2$ or —COOH group, the process of the invention consists in preparing first of all the corresponding fluorinated cyanated compound, in anhydrous medium, by means of the abovementioned fluorination process, which is followed by the hydrolysis of such compound in alkaline medium. The total hydrolysis followed by an acidification of the medium leads to a —COOH carboxylated compound, while the partial hydrolysis in alkaline medium leads to a —CONH$_2$ aminated compound.

In the case of the preparation of substituted α,α-difluoroalkylbenzenes wherein the substituent is a —COCl, the process of the invention consists in reacting the —COOH compound described above with thionyl chloride at 60° C. for 2 hours, evaporating the excess of SOCl$_2$ then distilling the residue.

In the case of the preparation of substituted α,α-difluoroalkylbenzenes wherein the substituent is a —CONR'$_2$ group, the process of the invention consists in reacting the acid chloride described above with double the theoretical amount of secondary amine R'$_2$NH. There is formed a precipitate of the amine chlorhydrate insoluble in the organic solvent; e.g. ether. The precipitate is filtered and the organic solvent is evaporated. The evaporation leads to the production of the sought amidated —CONR'$_2$ derivative.

In regard to the preparation of substituted α,α-difluoroalkylbenzene derivatives wherein the substituent is a —CHO group, the process of the invention consists in reacting a cyanated derivative as described above with an aluminum hydride, e.g. LiAlH(OC$_2$H$_5$)$_3$, hydrolyzing the mixture with 6 N sulfuric acid and evaporating the organic solvent, e.g. ether, in order to obtain the sought aldehydic —CHO derivative.

In order to obtain the substituted α,α-difluoroalkyl-benzene derivatives wherein the substituent is a —NHCOOR' group, the process consists in reacting the corresponding amide with bromine and an alcohol in alkaline alcoholate medium.

In order to obtain the substituted α,α-difluoroalkyl-benzene derivates wherein the substituent is a —CH$_2$OH group, the corresponding acid is reacted with LiAlH$_4$.

In order to obtain the substituted α,α-difluoroalkyl-benzene derivatives wherein the substituent is a CH$_2$NH$_2$ group, the corresponding nitrile is reacted with LiAlH$_4$ in excess.

For the amino esters of the type

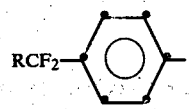

COO(CH$_2$)$_n$CONR'$_2$, the acid

is reacted with ClCOO(CH$_2$)$_n$NR'$_2$, n being 2 or 3.

In regard to preparing the substituted α,α-difluorotoluene derivatives, the basic molecule is the ortho, meta, para α,α-difluoromethylbenzonitrile which, through the ordinary processes that are mentioned above, leads to the following derivatives:

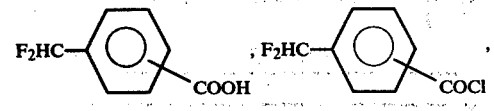

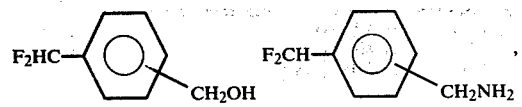

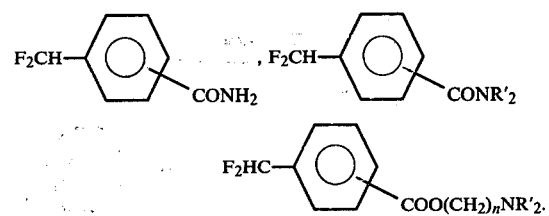

The general reactions for producing the compounds of the invention are summarized below, (a) for X equals —CN, —NO$_2$, —F, —Cl, —COOR', and

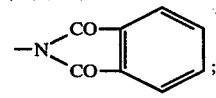

and R equals alkyl or aryl, the reaction is:

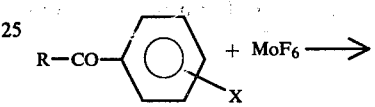

and for X equals —CN and R equals H the reaction is:

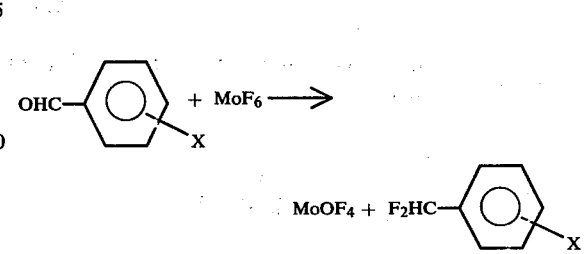

(b) for X equals —COOH or —CONH$_2$; and R equals alkyl or aryl, the reaction is:

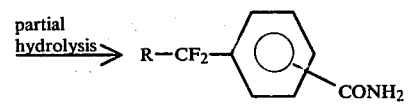

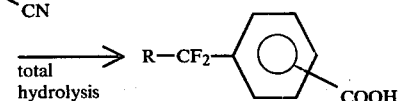

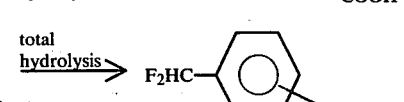

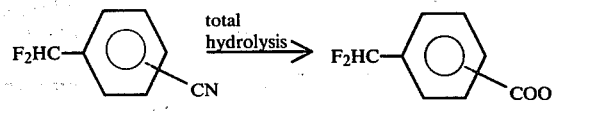

(c)

(d) for X equals COCl and R equals H, alkyl or aryl, the reaction is:

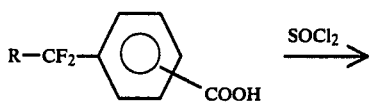

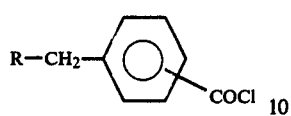

(e) for X equals CHO and R equals alkyl or aryl, the reaction is:

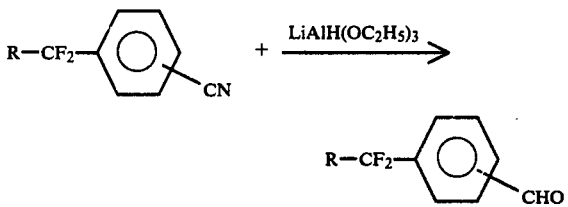

(f) for X equals —CONR'$_2$ and R equals H, alkyl or aryl, the reaction is:

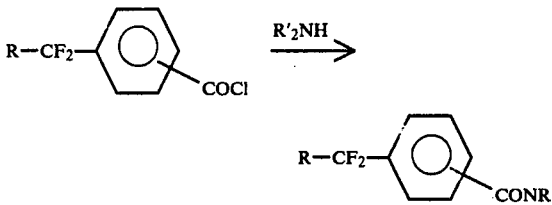

(g) for X equals NHCOOR' and R equals alkyl or aryl, the reaction is:

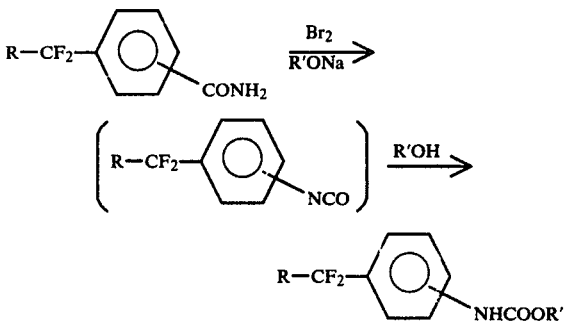

(h) for X equals CH$_2$OH and R equals H, alkyl or aryl, the reaction is:

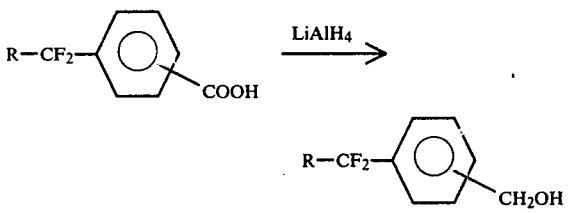

(i) for R equals H, alkyl or aryl; and X equals CH$_2$NH$_2$, the reaction is:

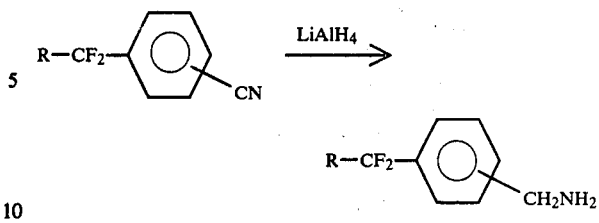

(j) for R equals H, alkyl or aryl; and X equals COO(CH$_2$)$_n$NR'$_2$ and where n is 2 or 3, the reaction is:

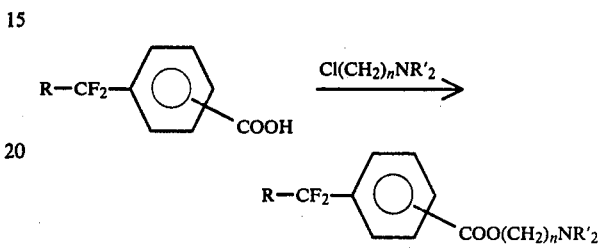

The molybdenum hexafluoride used as reagent during the fluorination stage can be prepared by any of the methods described in various papers, such as, for example, that of O. RUFF and E. ASHER (Z. ANORG. ALLG. CHEM. 196, 418, 1931) which involves the direct combustion of molybdenum in fluorine. Molybdenum hexafluoride is liquid at room temperature (b.p. 35° C. at atmospheric pressure); consequently it is very easy to use.

The solvent used for the fluorination stage is selected such that separation of the reagents and reaction products is maximized. The preferred solvent used is methylene chloride.

With regard to the preparation of compounds containing groups (X') not reactive with MoF$_6$, these are prepared directly by the MoF$_6$ reaction without later conversion.

The following series of new compounds have been thus obtained:

TABLE 1

| R | X' |
|---|---|
| CH$_3$ | p . Cl |
| CH$_3$ | p . CN |
| CH$_3$ | p . CO$_2$C$_2$H$_5$ |
| CH$_3$ | p . N(CO-)$_2$C$_6$H$_4$ |
| CH$_3$ | p . F |
| CH$_3$ | o . p . and m . NO$_2$ |
| CH$_3$ | m . CN |
| C$_2$H$_5$ | p . CN |
| phenyl | p . CN |
| H | p . and m . CN |

With reference to formulas (I) and (III) above, the following series of new compounds have been produced:

TABLE 2

| R | X | Initial Y |
|---|---|---|
| CH$_3$ | p . COOH | p . CN |
| CH$_3$ | p . CONH$_2$ | p . CN |
| CH$_3$ | p . NH . COOCH$_3$ | p . CN |
| CH$_3$ | p . CHO | p . CN |

TABLE 2-continued

| R | X | Initial Y |
|---|---|---|
| CH₃ | m . CO . OH | m . CN |
| CH₃ | p . COCl | p . CN |
| CH₃ | p . CH₂OH | p . CN |
| CH₃ | p . CH₂NH₂ | p . CN |
| H | p . CH₂NH₂ | p . CN |
| H | m . COOH | m . CN |
| CH₃ | p . CO—N(CH₂)₄O | p . CN |
| CH₃ | p . COO(CH)₂N(i-C₃H₇)₂ | p . CN |
| H | p . COOH | p . CN |

The following examples are given merely by way of an illustration and are in no way intended to limit the invention. The starting materials in these examples have been selected from aromatic aldehydes or ketones according to the definition given above in order to show the applicability of the instant process.

EXAMPLE 1 para-alpha, alpha-difluoroethyl-nitrobenzene 200 ml of $CH_2Cl_2$ freshly distilled over $P_2O_5$, 17 ml of $MoF_6$ (i.e. 0.2 mole) were introduced into a 500 ml flask equipped with a stirrer, a gas-inlet, a condenser and a drop funnel. The resulting yellow solution was cooled to 0° C. A slight stream of $BF_3$ gas was passed through the mixture and is maintained during the reaction. The mixture is then cooled to $-15°$ C. and 34 gm of p-$CH_3COC_6H_4NO_2$ (0.2 mole) in 100 ml of methylene chloride ($MoF_6$/CO group molar ratio=1) were introduced dropwise.

The solution became dark red. The temperature of the solution was allowed to rise to room temperature. It was then treated with 20 gm of dry NaF and stirred during one hour. It was filtered. The filtrate, the colour of which was blue was discoloured by stirring with $SiO_2$. The solution was evaporated and the resulting yellow residue submitted to chromatographic separation on a column of gel of silica in order to separate the constituents. Benzene is used as eluent. At the top of the column a product of the formula:

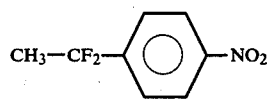

is recovered with a yield of 41%.
m.p.=48° C.

| Analysis | C | H | F |
|---|---|---|---|
| calculated | 51.33% | 3.74% | 7.48% |
| found | 50.83% | 3.81% | 7.25% |

EXAMPLE 2 para-alpha, alpha-difluoroethyl-cyanobenzene 150 ml of dry $CH_2Cl_2$ and 6 ml of $MoF_6$ (0.07 mole) were introduced into a 250 ml flask equipped with a stirrer, a gas-inlet, a condenser and a drop funnel. The solution was cooled to 0° C. and a slight stream of $BF_3$ gas was passed through it. The solution was then cooled to $-15°$ C. and 15.8 gm of p-$CH_3COC_6H_4CN$ in 50 ml of dry $CH_2Cl_2$ ($MoF_6$/CO group molar ratio=1) were introduced. The solution became red. Its temperature was then allowed to rise to room temperature and it was treated with 20 gm of dry NaF and the resulting blue solution was discoloured using $SiO_2$. After evaporation, the resulting residue can be either chromatographed on a column (gel of silica with $CH_2Cl_2$ as eluent) or distilled.

A yield of 42% of a product of formula

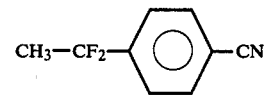

was obtained
b.p.₀₂=49° C.

| Analysis | C | H | F |
|---|---|---|---|
| Calculated | 64.67% | 4.19% | 8.39% |
| found | 64.42% | 4.02% | 7.81% |

EXAMPLE 3 meta-alpha, alpha-difluoroethyl-nitrobenzene

Example 1 was repeated with 12 ml of $MoF_6$ and 24 gm of m-$CH_3$-$COC_6H_4NO_2$ ($MoF_6$/CO group molar ratio=1). After chromatographic separation on the column of gel of silica (benzene as eluent) a product of formula:

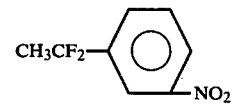

was obtained with a yield of 15%.
m.p.=48° C.

| Analysis | C | H | F |
|---|---|---|---|
| calculated | 51.33% | 3.74% | 7.48% |
| found | 50.95% | 3.53% | 7.10% |

EXAMPLE 4 ortho-alpha, alpha-difluoroethyl-nitrobenzene

Example 1 was repeated with 11 ml of $MoF_6$ and 22 gm of o-$CH_3COC_6H_4NO_2$ ($MoF_6$/CO group molar ratio=1). The separation of the constituents was carried out by chromatographic on a column of gel of silica (eluent: benzene 80—hexane 20) and a colourless liquid product of the formula

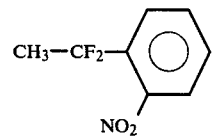

was obtained.
The product was identified by NMR spectroscopy of the proton and of fluorine.

EXAMPLE 5

N-(p-alpha,alpha-difluoroethylbenzene)phthalimide

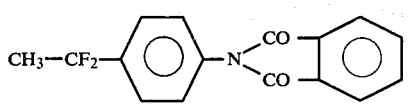

Example 1 was repeated with 20 ml of MoF$_6$ and 20 gm of N-(p-acetophenyl)phtalimide p-CH$_3$COC$_6$H$_4$N(CO)$_2$C$_6$H$_4$ (MoF$_6$/CO group molar ratio=1). By chromatographic separation of the constituents (eluent: CH$_2$Cl$_2$), a product of formula:

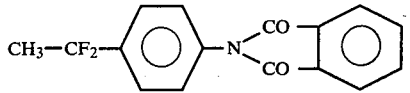

was obtained.
m.p. 205° C.

| Analysis | C | H | F |
|---|---|---|---|
| calculated | 66.90% | 3.83% | 4.88% |
| found | 66.30% | 4.27% | 4.30% |

EXAMPLE 6 para-alpha, alpha-difluoroethyl-fluorobenzene

Example 2 was repeated with 11 ml of MoF$_6$ and 19 gm of p-CH$_3$COC$_6$H$_4$F (McF$_6$/CO group molar ratio=1). After distillation of the reaction mixture, a product of formula:

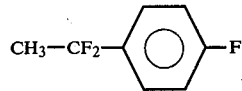

was obtained.
b.p.$_{10}$=70° C.
n$_D^{20}$=1.4355
This product was identified by NMR spectroscopy of the proton and of fluorine.

EXAMPLE 7 para-alpha, alpha-difluoroethyl-chlorobenzene

Example 2 was repeated with 14 ml of MoF$_6$ and 26 gm of p-CH$_3$COC$_6$H$_4$Cl (MoF$_6$/CO group molar ratio=1). After distillation of the reaction mixture a product of formula:

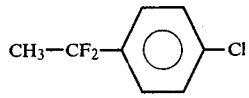

was obtained.
b.p.$_8$=90° C.
This product was identified by NMR spectroscopy of the proton and of fluorine.

EXAMPLE 8 para-alpha, alpha-difluoroethyl ethyl benzoate

Example 1 was repeated with 7 ml of MoF$_6$ and 13.6 gm of p-CH$_3$-COC$_6$H$_4$COOC$_2$H$_5$ (MoF$_6$/CO group molar ratio=1). There was obtained, after chromatography on the column of gel of silica (eluent: CH$_2$Cl$_2$) a yield of 12.5%, with respect to the theoretical amount, of a product of formula:

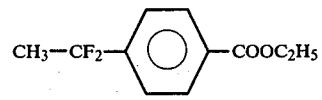

in the form of a colourless liquid.

EXAMPLE 9 para-alpha, alpha-difluoropropyl-cyanobenzene

Example 1 was repeated with 4.5 ml of MoF$_6$ and 8 gm of p-C$_2$H$_5$-COC$_6$H$_4$CN (MoF$_6$/CO group molar ratio=1). There was obtained, after chromatography on the gel column of silica (eluent: benzene 50-hexane 10) a liquid product of the formula:

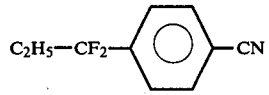

n$_D^{20}$=1.4884; yield=16.5%

| Analysis | C | H | F |
|---|---|---|---|
| calculated | 66.00% | 4.96% | 7.73% |
| found | 65.26% | 4.48% | 7.44% |

EXAMPLE 10 meta-alpha, alpha-difluoroethyl-cyanobenzene

Example 1 was repeated with 5 ml of MoF$_6$ and 6 gm of m-CH$_3$COC$_6$H$_4$CN (MoF$_6$/CO group molar ratio=1). There is obtained, after chromatography on the gel column of silica (eluent: benzene 80-hexane20) with a yield of 33%, a liquid product having the formula:

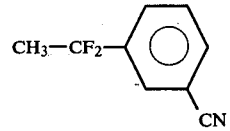

n$_D^{20}$=1.4825

| Analysis | C | H | F |
|---|---|---|---|
| calculated | 64.67% | 4.19% | 8.39% |
| found | 63.80% | 3.75% | 8.12% |

EXAMPLE 11 difluorophenyl [4-cyanophenyl], methane

Example 1 was repeated with 5 ml of MoF$_6$ and 6 gm (MoF$_6$/CO group molar ratio=1) of

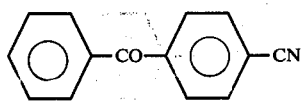

After chromatography on the gel column of silica (eluent: benzene) a yield of 27% with respect to the theoretical amount of

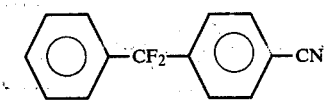

was obtained.
m.p.=40° C.

| Analysis | C | H | F |
|---|---|---|---|
| calculated | 73.35% | 3.96% | 6.11% |
| found | 73.53% | 3.43% | 6.09% |

EXAMPLE 12 meta-alpha, alpha-difluoro-cyanotoluene

Example 1 was repeated with 5 ml of MoF$_6$ and 7 gm of meta-cyanobenzaldehyde (MoF$_6$/CO group molar ratio=1). After chromatography on the gel column of silica (eluent: benzene) a liquid product having the formula:

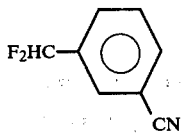

was obtained with a yield of 20%.

| Analysis | C | H | F |
|---|---|---|---|
| calculated | 62.75% | 3.29% | 9.15% |
| found | 61.90% | 2.81% | 8.23% |

EXAMPLE 13

Example 1 was repeated with 5 ml of MoF$_6$ and 7 gm (MoF$_6$/CO group molar ratio=1) of

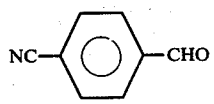

After chromatography on the gel column of silica (eluent: CHCl$_3$), 1.65 gm of

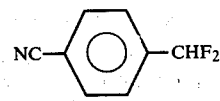

was obtained.
n$_D^{10}$=1.4990

| Analysis | C | H | F |
|---|---|---|---|
| calculated | 62.74% | 3.29% | 9.15% |
| found | 61.56% | 3.26% | 8.26% |

EXAMPLE 14 para α,α-difluoroethyl benzoic acid.

7 gm of

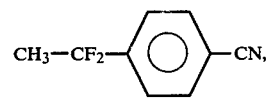

4 gm of sodium hydroxide and 100 ml of water at 80°-90° C. were reacted during about 24 h. A clear solution was obtained. The heating was stopped when no further ammonia evolved. The cooled solution was then acidified with concentrated HCl. The formed white precipitate was washed with water and dried under vacuum. 7 gm of

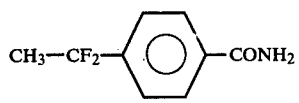

was thus obtained.
MP=182° C.; yield=90%.

EXAMPLE 15 para α,α-difluoro ethyl benzamide.

5 gm of p-CH$_3$CF$_2$C$_6$H$_4$CN, 200 ml of an aqueous solution of H$_2$O$_2$ at 3% and 10 ml of an aqueous solution of NaOH at 25% were reacted at 60° C. during 4 hours. A white precipitate was progressively formed. The reaction medium was then cooled, filtered, washed with water and dried under vacuum. 5.5 gm of

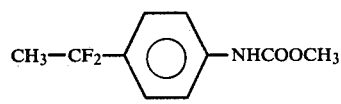

were obtained.
M.P.=170° C.; yield=99%.

EXAMPLE 16

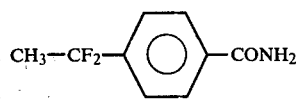

(methyl para-α,α-difluoroethylphenylcarbamate)

In a mixture of 1.7 gm of

CH$_3$—CF$_2$—⟨phenyl⟩—CONH$_2$ in 10 ml of pure methanol, there was added a solution obtained from 0.46 gm of sodium and 15 ml of methanol.

1.6 gm of bromine were then added and the mixture was heated 10 minutes at 60° C. The colourless solution was neutralized with acetic acid. It was evaporated under vacuum and the residue was washed with water in order to eliminate any traces of sodium bromide which may be present. The theoritical yield in

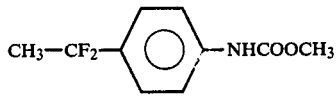

was obtained.
M.P.=95° C.

EXAMPLE 17 para-α,α-difluoroethyl benzaldehyde

In a mixture obtained from 1.15 gm of LiAlH₄, 2.2 gm of CH₃COOC₂H₅ and 30 ml of anhydrous ether (exothermic reaction), 5 gm of p-CH₃-CF₂C₆H₄CN in 10 ml of ether were slowly added. The reaction is lightly exothermic. The solution was then cautiously treated with 30 ml of 6 N sulphuric acid. The ether layer was washed with water, separated and dried. On evaporation there was obtained, with a yield of 20%, a yellow liquid of

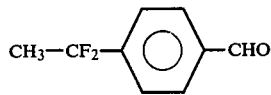

which crystallized very slowly.

EXAMPLE 18 meta-α,α-difluoroethyl benzoic acid

Example 14 was repeated with 0.5 gm of m-CH₃-CF₂C₆H₄ CN. A white solid (0.5 gm) was obtained. M.P.=109°-110° C. Formula:

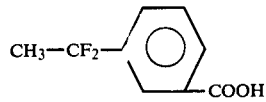

EXAMPLE 19 para-α,α-difluoroethyl benzoic acid chloride 7 gm of

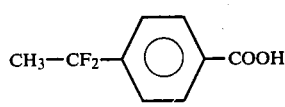

were reacted with 30 ml of SOCl₂ at 60° C. during 2 hours. The resulting solution was evaporated under vacuum. The residue was distilled to give 5 gm of

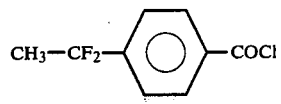

B.P.₀.₁=45° C.

EXAMPLE 20

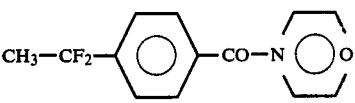

4 gm of

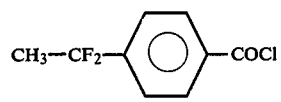

were poured in a solution of 3.5 gm of morpholine in 50 ml of anhydrous ether. A precipitate of morpholine hydrochloride was formed. The resulting solution was filtered and evaporated. The residue was washed with water and dried. 4 gm of

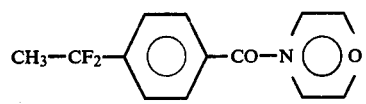

were obtained.
M.P. 128° C.

This product can be recrystallized from ethanol.

EXAMPLE 21

Example 14 was repeated with 0.5 gm of

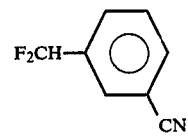

and 0.5 gm of

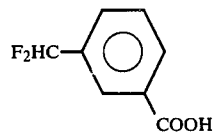

was obtained.
M.P.=128°-129° C.

EXAMPLE 22 para-α,α-difluoroethyl benzylic alcohol 1.8 gm of p-CH₃CF₂C₆H₄ COOH were dissolved in 25 ml of ether and the reaction is alloved to proceed, during one hour, at room temperature, with a suspension of 0.5 gm of LiAlH₄ in 25 ml of ether. The excess of LiAlH₄ is hydrolized with diluted hydrochloric acid.

After decantation, the ether layer is washed with water, dried on Na₂SO₄ and then evaporated; the liquid residue is chromatographied on a column of gel of silica (with benzene as eluant). A yellow liquid (0.8 gm) was obtained. The formula of this produit is: p-CH₃-CF₂-C₆H₄-CH₂OH.

Yield = 48%.

EXAMPLE 23 diisopropyl aminoethanol para-α,α-difluoroethylbenzoate 1.9 gm of p-CH₃CF₂C₆H₄COOH were reacted with 1.6 gm of ClCH₂CH₂N (i-C₃H₇)₂ in 50 ml of isopropanol (i-C₃H₇OH). The solution was refluxed for one hour. The isopropanol was then evaporated under vacuum. The residue was washed with water to eliminate any starting compound. The resulting crystals of the resulting hydrochloride which are insoluble in ether were then treated with a 5% Na₂CO₃ aqueous solution, followed by an ether extraction. The ether solution was then dried on Na₂SO₄. The ether was evaporated and 1.9 gm of a slightly viscous yellow liquid of the formula:

p-CH₃CF₂C₆H₄COOCH₂CH₂N(i-C₃H₇)₂ were recovered.

Yield: 60%.

EXAMPLE 24 para-α,α-difluoroethyl benzylic amine 1.67 gm (1/100 mole) of

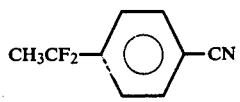

and 25 ml of anhydrous ether were poured in a mixture of 0.5 gm of LiAlH₄ and 25 ml of anhydrous ether. The reaction is slightly exothermic. A reflux heating was carried out for 8 hours. The excess of LiAlH₄ was then destroyed with distilled water. The ether layer was washed with water and dried on Na₂SO₄. The hydrochloride of the amine was precipitated by passing through the ether solution a stream of HCl gas until saturation was obtained. The resulting precipitate was then washed with ether and dried under vacuum.

1.25 gm of

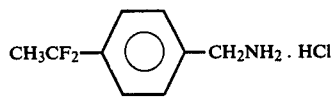

were thus obtained.

EXAMPLE 25 para-difluoromethyl benzylic amine

As described in example 23, 4.6 gm of

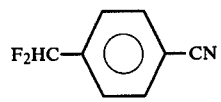

were reacted with 2 gm of LiAlH₄ in 50 ml of ether. 2.6 gm of a white product corresponding to the following formula were thus obtained:

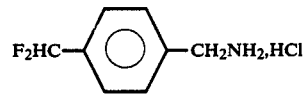

EXAMPLE 26

Example 14 was repeated with 0.5 gm of

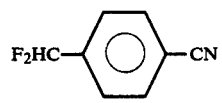

and there was obtained 0.45 gm of:

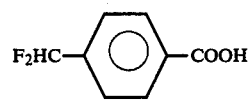

What is claimed is:

1. Process for preparing an organic compound of the formula

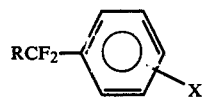

wherein R is H, lower alkyl or phenyl and X is a group capable of reacting with MoF₆ and selected from Lewis bases and groups possessing labile hydrogen atoms, by fluorinating a starting compound of the formula

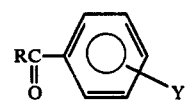

wherein Y is a group incapable of reacting with MoF₆ under the following conditions, but is capable of conversion to X by conventional synthesis, comprising reacting substantially anhydrous MoF₆ with said compound

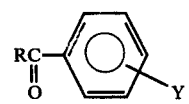

under anhydrous conditions in solution in an organic solvent inert with respect to the reactants at a temperature of about −20° C. to about +40° C. under an inert atmosphere to obtain the intermediate product

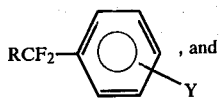

reacting said intermediate product using a conventional organic synthesis to obtain said organic compound

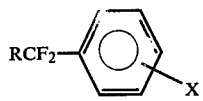

2. A process in accordance with claim 1 wherein Y is CN and said conventional organic synthesis comprises alkaline hydrolysis to obtain said organic compound wherein X is —$CONH_2$ or —COOH.

3. A process in accordance with claim 2 wherein Y is CN and said conventional organic synthesis comprises total alkaline hydrolysis, followed by acidification, followed by reaction with thionyl chloride to obtain said organic compound wherein X is —COCl.

4. A process in accordance with claim 1 or 3 wherein X is a —$CONR'_2$ group (where R' is an alkyl or aryl radical) comprising reacting the corresponding acid chloride (X=—COCl) with a secondary amine ($R'_2NH$).

5. A process in accordance with claim 1 wherein X is a —CHO group and R is a lower alkyl or phenyl group, comprising reacting the corresponding compound in the formula of which X is a —CN group with the aluminum hydride $LiAlH(OC_2H_5)_3$ and hydrolyzing the resulting mixture.

6. A process in accordance with claim 1 wherein R is a lower alkyl or phenyl radical and X is a —NHCOOR' group (where R' is an alkyl or aryl radical), comprising reacting the corresponding amide compound (X=—$CONH_2$) with bromine and a R'OH alcohol in alkaline alcoholate medium.

7. A process in accordance with claim 1 wherein R is hydrogen or a lower alkyl or phenyl group and X is a —$CH_2OH$ group, comprising reacting the corresponding compound in the formula of which X is the —COOH group with $LiAlH_4$.

8. A process in accordance with claim 1 wherein R is hydrogen or a lower alkyl or phenyl group and X is a —COO$(CH_2)_n NR'_2$ group (n being 2 or 3 and R' an alkyl or aryl radical), comprising reacting the corresponding carboxylic compound with Cl$(CH_2)_n NR'_2$.

9. A process in accordance with claim 1 wherein R is hydrogen or a lower alkyl or phenyl group and X is a —$CH_2NH_2$ group comprising reacting the corresponding cyanated compound with $LiAlH_4$.

* * * * *